(12) United States Patent
Ghadiali et al.

(10) Patent No.: US 11,493,492 B2
(45) Date of Patent: Nov. 8, 2022

(54) COMPENSATION OF ENVIRONMENTALLY-INDUCED DRIFT IN AN ELECTROCHEMICAL CARBON-MONOXIDE SENSOR

(71) Applicant: Google LLC, Mountain View, CA (US)

(72) Inventors: Aditya Ghadiali, Freemont, CA (US); Kunal Kishore Bajaj, Freemont, CA (US)

(73) Assignee: Google LLC, Mountain View, CA (US)

( * ) Notice: Subject to any disclaimer, the term of this patent is extended or adjusted under 35 U.S.C. 154(b) by 903 days.

(21) Appl. No.: 16/273,327

(22) Filed: Feb. 12, 2019

(65) Prior Publication Data

US 2020/0256839 A1    Aug. 13, 2020

(51) Int. Cl.
*G01N 33/00*    (2006.01)

(52) U.S. Cl.
CPC ....... *G01N 33/0034* (2013.01); *G01N 33/004* (2013.01); *G01N 33/0006* (2013.01)

(58) Field of Classification Search
CPC ............. G01N 33/0034; G01N 33/004; G01N 33/0006; G01N 33/0062; G01N 33/0063; G01N 33/0032; G01N 33/0031; G01N 33/48707; G01N 1/2273; G01N 21/3504; G01N 2201/1211; F24F 11/30; F24F 2110/10; F24F 2110/20; F24F 2110/66; G01K 7/42; G01W 1/00; Y02A 50/20
USPC ........... 73/1.03, 23.2, 25.03, 29.01; 340/521, 340/632; 700/1, 266, 276; 702/1, 3, 19, 702/22–24, 30, 99, 104, 116, 127, 130, 702/182, 188
See application file for complete search history.

(56) References Cited

U.S. PATENT DOCUMENTS

| | | | | |
|---|---|---|---|---|
| 6,128,945 A | * | 10/2000 | Shioiri | G01N 27/122 73/31.06 |
| 9,213,016 B1 | | 12/2015 | Stetter | |
| 2010/0050737 A1 | * | 3/2010 | Wolters | G01N 30/8665 73/23.35 |
| 2011/0061371 A1 | * | 3/2011 | Cavataio | F02M 26/35 60/297 |
| 2018/0156766 A1 | * | 6/2018 | Zeng | G01N 33/004 |
| 2020/0015707 A1 | * | 1/2020 | Ratto | G01N 33/497 |

FOREIGN PATENT DOCUMENTS

| | | | | | |
|---|---|---|---|---|---|
| CN | 1213082 A | * | 4/1999 | ......... | G01N 27/122 |
| WO | WO-0137231 A2 | * | 5/2001 | ......... | G01N 33/0032 |

OTHER PUBLICATIONS

Buck, Amy Leigh. Steady State and Transient Response Characteristics of Commercial Carbon Monoxide Sensors. May 4, 2014. (80 pages).
KWJ Engineering Inc. X-144 ICOM. [online]. [retrieved Jan. 30, 2019]. Retrieved using Internet <URL: https://www.sata.com/uploads/tx_pxspecialcontent/X144_ICOM_Instructions.pdf/> (2 pages).

* cited by examiner

*Primary Examiner* — Jeffrey P Aiello
(74) *Attorney, Agent, or Firm* — Kilpatrick Townsend & Stockton LLP

(57) ABSTRACT

Methods of the disclosed subject matter provide compensation for sensor drift in a hazard detection device having a plurality of sensors coupled to a processor to determine that a carbon monoxide sensor is drifting and to compensate for the drift by calculating a corrected carbon monoxide measurement value based on the ambient environmental conditions.

30 Claims, 7 Drawing Sheets

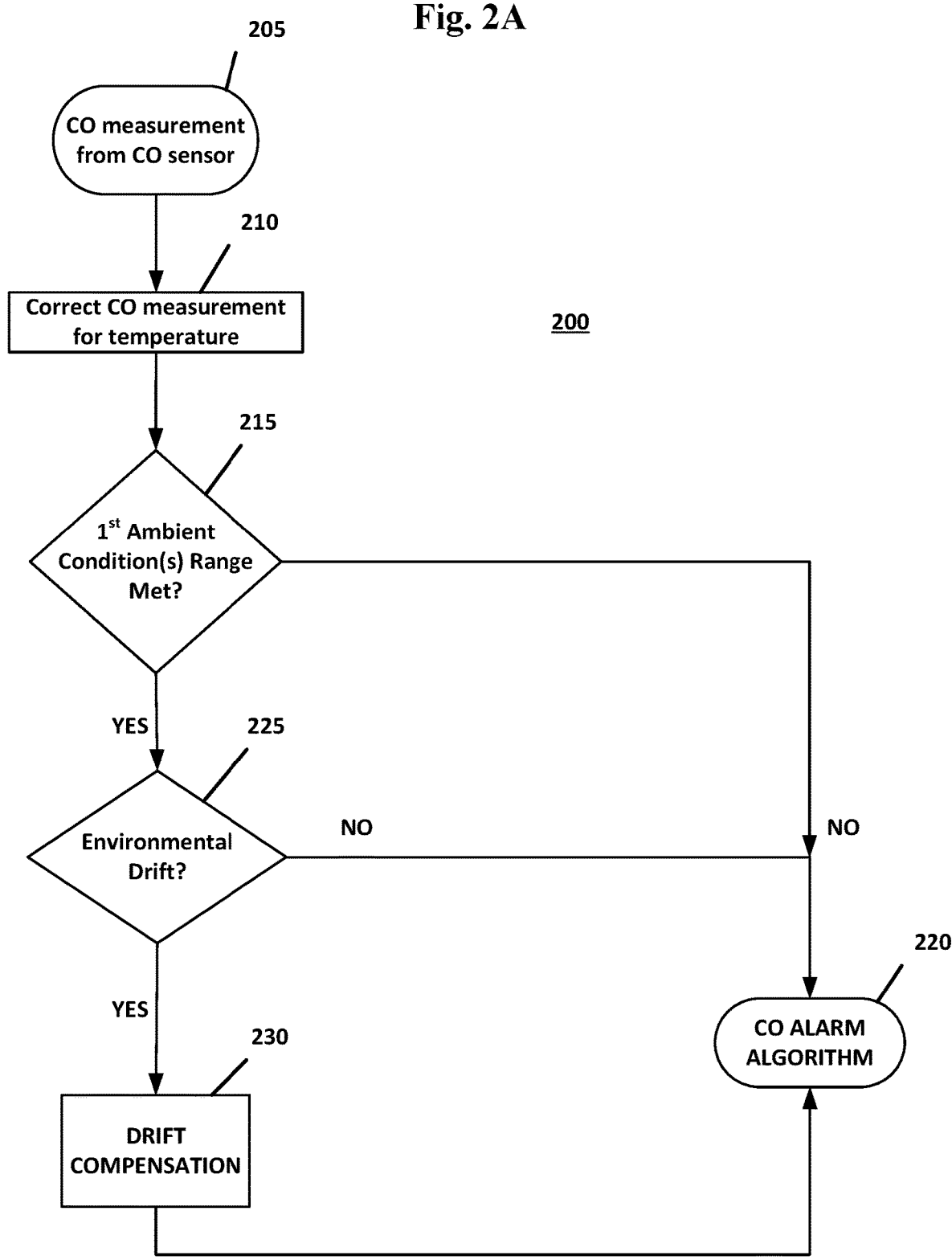

COMPENSATION OF ENVIRONMENTALLY-INDUCED DRIFT IN AN ELECTROCHEMICAL CARBON-MONOXIDE SENSOR

BACKGROUND

Electronic sensors are known to be susceptible to drift, which occurs when the sensor output varies independently of or disproportionately to the physical property being measured. This variation results in inaccurate and/or unstable measurements, thereby reducing the ability of the associated system to correctly respond. In the context of smoke and carbon monoxide (CO) detection devices, sensor drift can cause the device to fail to alert or to alert needlessly.

Ambient environmental factors such as vibration, contamination, temperature, and humidity may exacerbate a sensor's tendency to drift. To mitigate drift and the resulting loss of sensor accuracy, manufacturers employ various techniques. For example, a manufacturer may physically isolate the sensing element from the ambient environment, at the expense of reduced sensitivity and slowed response. Alternatively, a manufacturer may attempt to regulate localized environmental conditions, such as temperature, to stabilize the degree of drift in exchange for increased device cost and complexity. Alternatively or in addition to addressing the problem from a mechanical standpoint, a manufacturer may provide data outlining the anticipated drift of a sensor under various ambient environmental conditions, which may be used by a system architect to compensate for the expected sensor drift.

BRIEF SUMMARY

According to an embodiment of the disclosed subject matter, a hazard detection device includes a humidity sensor, a temperature sensor, a carbon monoxide (CO) sensor, and a processor, where the processor may determine that the CO measurement indicates a drift in measurement by the CO sensor, and calculates a corrected CO measurement based on the CO measurement, the ambient relative humidity, and/or the ambient temperature. The device generates an alarm based on the corrected CO measurement. The processor may determine that the CO measurement indicates a drift in measurement by determining that the ambient temperature falls within a first temperature range and corrects based on a first compensation factor. The processor may additionally determine that the ambient temperature falls within a second temperature range, and determine whether the drift in measurement meets a threshold, and if so, calculating the corrected CO measurement based on the compensation factor. The drift in measurement may be based on a rate of rise of the CO measurement or a difference between the CO measurement and a predetermined baseline measurement. If the threshold has not been met, the processor calculates the CO measurement based on a first correction value when the ambient temperature falls within a third temperature range, the first correction value based on the amount of time the CO sensor has been operating in the third ambient temperature range. Alternatively, if the threshold has not been met, the processor calculates the corrected CO measurement based on a second correction value when the ambient temperature falls within a fourth temperature range, the second correction value based on the amount of time the CO sensor has been operating in the fourth ambient temperature range. Alternatively, if the threshold has not been met, the processor calculates the corrected CO measurement based on a third correction value when the ambient temperature falls within a fifth range, the third correction value is based on the amount of time the CO sensor has been operating in the fifth ambient temperature range. The processor may determine that the CO measurement indicates a drift in measurement by the CO sensor by determining that the ambient relative humidity falls within a first humidity range and/or a within a second humidity range.

Additional features, advantages, and embodiments of the disclosed subject matter may be set forth or apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate embodiments of the disclosed subject matter and together with the detailed description explain the principles of embodiments of the disclosed subject matter. No attempt is made to show structural details in more detail than may be necessary for a fundamental understanding of the disclosed subject matter and various ways in which it may be practiced.

FIGS. 2A and 2B are a flow diagram illustrating an example of a method for identifying and compensating for drift of a sensor according to an embodiment of the disclosed subject matter.

DETAILED DESCRIPTION

As previously disclosed, environmental sensors often exhibit various levels of drift. Sensor manufacturers may provide technical information that describes the extent of drift that can be expected, the conditions under which drift will occur, or the like. However, such information may be inaccurate or may change over time or with different sensors. Therefore, it is desirable to compensate for sensor drift in a hazard detection device, thereby ensuring that the system will provide an alert at the correct time under the circumstances.

The present subject matter discloses a hazard detection device and method for compensating for the effects of elevated environmental conditions on measured values from an electrochemical sensor. The disclosed hazard detection device and associated method may be applicable to drift compensation for a broad range of sensors, although the example embodiments disclosed herein refer to a carbon monoxide (CO) detection device utilizing at least a CO sensor. In particular, the disclosed compensation method may be especially applicable to CO sensors lacking a water reservoir to regulate the ambient relative humidity level.

Drift compensation may be achieved, for example, by using one or more peripheral sensors of the hazard detection device to determine when the hazard detection device is operating within a specific range or ranges of ambient environmental conditions and whether the rate of rise of the CO has reached a threshold level. Initially, the method may check for drift using a baseline measurement. Thereafter, the rate of rise of the CO measurement along with the relative humidity and ambient temperature may be used to determine whether changes in the CO measurement are due to real accumulation of CO and/or environmentally-induced drift. At each ambient environmental range, the method may compensate for sensor drift by calculating a substitute CO measurement value that includes an adjustment for the degree of expected drift of the CO sensor. More or less compensation may be provided according to the length of time that the hazard detection device has been operating within a particular ambient environmental range, the rate at which the CO measurement is changing, predetermined sensor baseline measurements, and other relevant factors.

Figure 1:
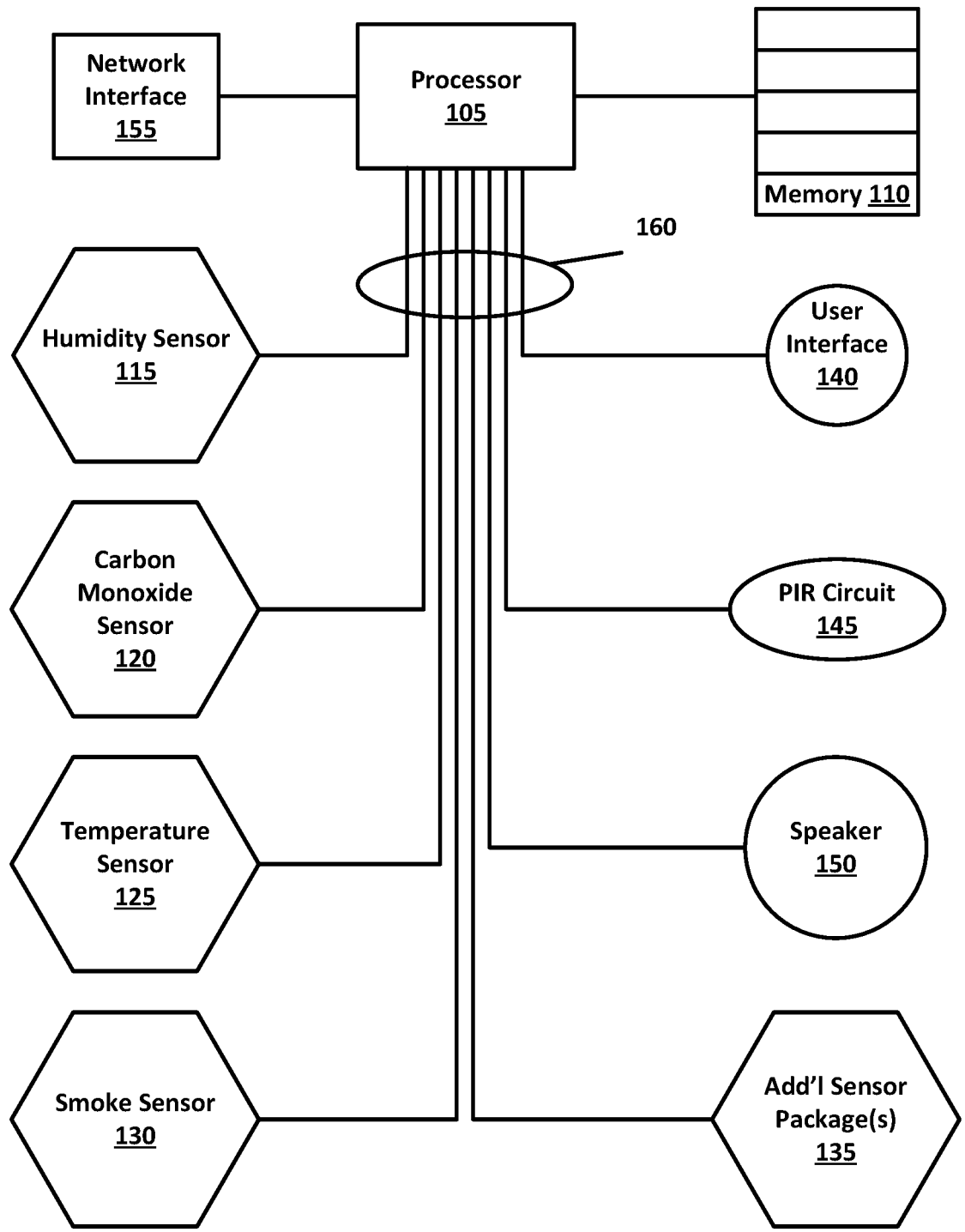
FIG. 1 is a logical diagram of a hazard detection device according to an embodiment of the disclosed subject matter.

FIG. 1 illustrates a logical overview of an example hazard detection device 100. The hazard detection device 100 may include a processor 105 that controls operations of the hazard detection device 100. The processor 105 may execute instructions stored on a computer-readable memory 110. The memory 110 or another memory in the hazard detection device 100 may also store data collected from the sensors 115-130 and/or additional sensor packages 135 provided directly or indirectly via network interface 155. User interface (UI) 140 may provide information and/or receive input from a user of the hazard detection device 100. Passive infrared (PIR) circuit 145 may interface with a PIR sensor used to detect human presence. Speaker 150 may provide an audible alarm when a condition is detected by one or more sensors 115-130 or based upon data received via network interface 155. The specific components and arrangement of a hazard detection device as shown in FIG. 1 are merely illustrative, and it will be understood that CO detectors and other sensors disclosed herein and the associated techniques also may be used with other devices and device configurations without departing from the scope of the present disclosure. For example, other physical arrangements may be used, and the hazard detection device may include or exclude various other sensors and components than those shown.

Figure 2B:
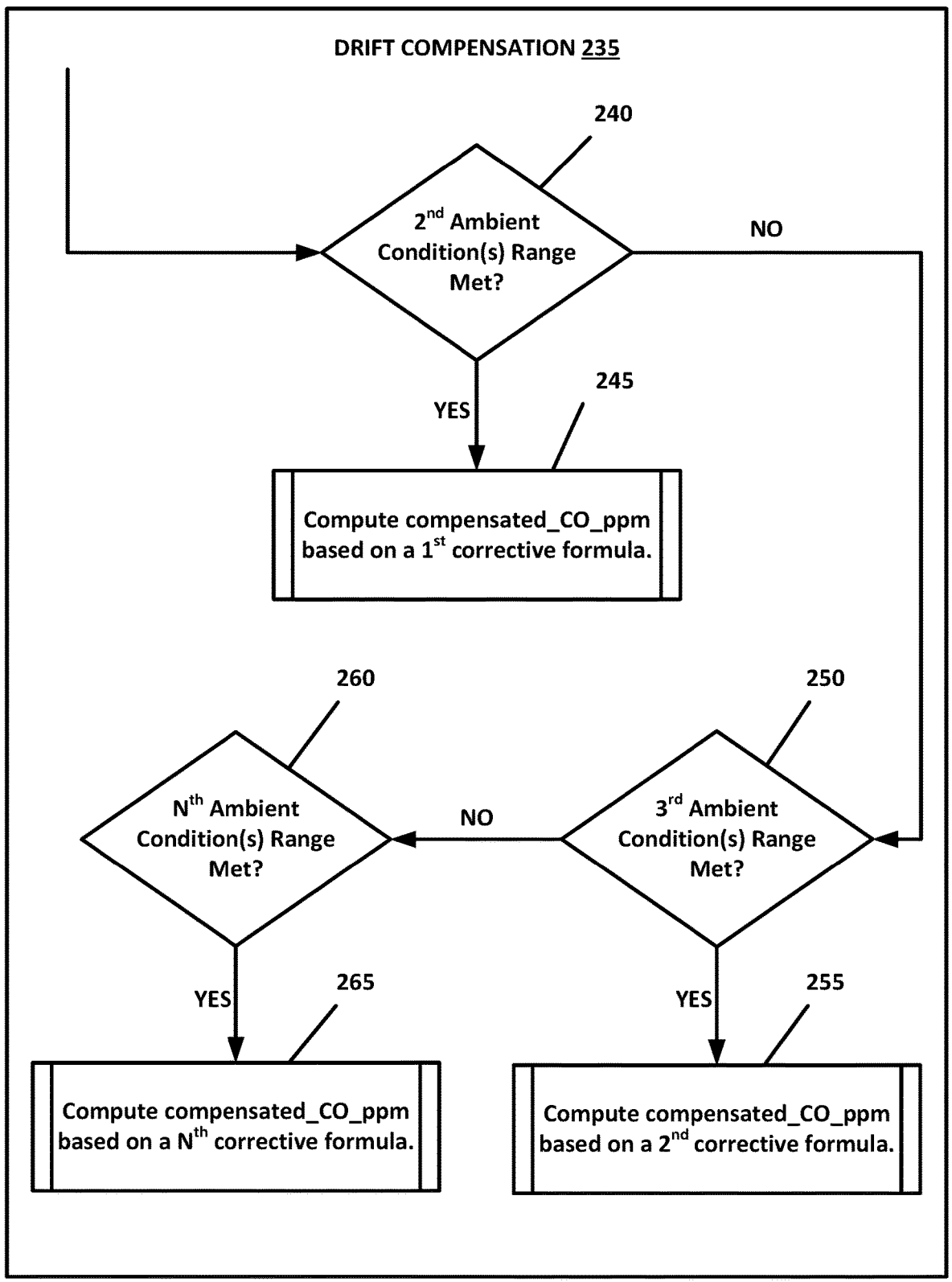

FIGS. 2A and 2B are flow diagrams illustrating an example of a method 200 for compensating for drift of a CO sensor using a baseline correction approach. In the method 200 as shown in FIG. 2A, a CO measurement 205 is obtained from the CO sensor 120. The measurement 205 may be received by the processor 105 and may be a voltage reading, a current reading, a packetized message, or other means of signaling known in the art. The CO measurement 205 may be corrected for temperature at step 210 by applying a compensation factor to the current CO measurement 205. The compensation factor used to calculate the corrected measurement may be supplied by the sensor manufacturer or determined experimentally. This initial compensation or similar adjustments may be performed regardless of any drift, such as where it is known that a particular sensor operates differently within different environmental conditions.

In some cases, it may be determined that a sensor is susceptible to drift when it is operating within a particular range of environmental conditions. For example, a CO sensor as disclosed herein may be more susceptible to measurable drift when the ambient temperature and/or humidity are relatively high. Accordingly, at step 215, processor 105 may determine whether the current ambient conditions fall within a first range, such as a range within which it is expected that the sensor may be susceptible to drift. Ambient conditions may include, for example, the ambient temperature and the ambient relative humidity. As a specific example, it may be expected that the sensor will not exhibit drift when either the ambient temperature is 26° C. or less or the ambient relative humidity is 60% or less. In this example, then, the processor 105 will proceed to carry out the CO alarm algorithm 220 when such conditions are present. The alarm algorithm 220 may vary based on country-specific safety standards in terms of the quantity of CO required to raise an alarm. If it is determined that ambient conditions are such that the sensor may be expected to exhibit appreciable environmental drift, then the method may continue to determine the degree of environmental drift present. Continuing the example above and as shown in FIG. 2A, if the ambient temperature is greater than 26° C. and the ambient relative humidity is greater than 60%, the method proceeds to step 225 to determine whether the CO sensor is experiencing appreciable environmental drift.

In an embodiment, the baseline drift of a sensor may be computed in step 225 by subtracting a baseline CO sensor measurement from the temperature-corrected measurement determined in step 210. The baseline CO sensor measurement is preferably obtained by recording the CO sensor reading when there is no CO present in the environment, such as during manufacture of the device. A threshold may be determined for comparing with the calculated baseline drift. The threshold amount, for example, may be two parts-per-million (ppm), representing the minimum amount of offset that may indicate environmental drift and warrant compensation measures. More generally, the threshold amount may be determined based upon properties of a specific sensor, such as via experimental testing or manufacturer data, or it may be set based upon the expected environmental conditions where the sensor is expected to be used. Additionally in step 225, the rate at which the CO sensor 120 reading is rising may be assessed to determine whether it is less than a selected threshold amount. For example, the threshold amount may be selected to fall within a range of 6-16 parts per billion per second (ppb/s). Should the baseline drift exceed the threshold amount while the rate of rise simultaneously falls below the selected threshold, it may be presumed that environmental drift is occurring, and the method proceeds to the drift compensation block 230. Otherwise, it may be presumed that the CO sensor 120 reading is accurate, and the method proceeds to the CO alarm algorithm 220.

FIG. 2B illustrates the details of drift compensation block 230. Once the processor 105 enters drift compensation block 230, any number of determinations may be made of the ambient environmental conditions, and any number of corrective formulas may be applied based on the outcome of those determinations. For example, a first determination 240 may be made as to whether the ambient temperature is between 26° C. and 30° C., and whether the ambient relative humidity is greater than 75%. If so, the CO sensor measurement is recalculated at step 245 according to formula (1) shown below. Step 245 may compute a new drift-compensated CO measurement by subtracting the smaller of, i.e., the minimum, of the baseline drift computed in step 225 (drift_ppm) and an upper limit value (upper_limit) from the temperature-corrected CO measurement computed in step 210 (temperature corrected_ppm). By using the minimum function, the algorithm may be prevented from overcompensating during elevated environmental conditions. The computation performed in step 245 to determine the new drift-compensated CO measurement (compensated_CO_ppm) may be expressed as follows:

$$\text{compensated\_CO\_ppm} = \text{temperature\_corrected\_ppm} - \text{MIN}(\text{drift\_ppm}, \text{upper\_limit}) \quad (1)$$

The upper_limit value in formula (1) above for the temperature range tested in step 240 may be set to 2 ppm. The upper_limit value may establish a maximum amount of compensation for drift and thereby reduce the likelihood of overcompensation. Overcompensation for drift may result in the CO detection device failing to alert when the actual CO concentration has reached a dangerous level. The upper_limit value may be determined experimentally for each temperature and relative humidity by recording a maximum amount of observed drift and by setting the upper_limit to the same value. For example, at a temperature of 40° C., the maximum drift for a statistically significant set of sample CO sensors may be experimentally found to be 18, 10, 9, and 7.5 ppm at 93%, 84%, 81%, and 78% relative humidity, respectively. Accordingly, a lookup table may be constructed that associates the observed maximum drift amount at each temperature and relative humidity measurement. The lookup table may list each temperature and humidity in 0.1, 1, 5, 10, or any other unit increment according to the granularity desired. Alternatively or in addition, where observable measurements have not been obtained, the expected maximum drift at a temperature and relative humidity may be interpolated or extrapolated based on the existing drift data. Every CO sensor may exhibit differing drift characteristics, and a statistically significant set of CO sensors, such as 60 or more, may be tested to better understand the range of variation. Once the expected maximum amount of drift can be determined for each temperature and relative humidity, a corresponding upper_limit value may be selected such that the processor 105 cannot compensate for more sensor drift than would be expected at the temperature and relative humidity.

More generally, techniques as disclosed herein may compensate for observed or expected drift when the sensor is operating in an environment in which drift is expected to occur by adjusting the measured CO value by a fixed amount, a computed drift amount, or a combination thereof.

This basic process of determining ambient operating conditions of the sensor and making an adjustment accordingly may be repeated any number of times. For example, referring back to FIG. 2B, a second determination 250 may be made as to whether the ambient temperature is between 30° C. and 35° C., and whether the ambient relative humidity is greater than 75%. If so, the CO sensor measurement is recalculated at step 255 according to formula (2) shown below. Step 255 may compute a new drift-compensated CO measurement by subtracting the smaller of, i.e., the minimum, of the drift computed in step 225 (drift_ppm) and an upper limit value (upper_limit) from the temperature-corrected CO measurement computed in step 210 (temperature_corrected_ppm). The computation performed in step 245 to determine the new drift-compensated CO measurement (compensated CO_ppm) may be expressed as follows:

$$\text{compensated CO\_ppm} = \text{temperature\_corrected\_ppm} - \text{MIN}(\text{drift\_ppm}, \text{upper\_limit}) \quad (2)$$

The upper_limit value in formula (2) above for the temperature range tested in step 250 may be set to 5 ppm. The upper_limit value may establish a maximum amount of compensation for drift and thereby reduce the likelihood of overcompensation. Overcompensation for drift may result in the CO detection device failing to alert when the actual CO concentration has reached a dangerous level. The upper_limit value may be determined experimentally for each temperature and relative humidity by recording a maximum amount of observed drift and by setting the upper_limit to the same value. For example, at a temperature of 40° C., the maximum drift for a statistically significant set of sample CO sensors may be experimentally found to be 18, 10, 9, and 7.5 ppm at 93%, 84%, 81%, and 78% relative humidity, respectively. Accordingly, a lookup table may be constructed that associates the observed maximum drift amount at each temperature and relative humidity measurement. The lookup table may list each temperature and humidity in 0.1, 1, 5, 10, or any other unit increment according to the granularity desired. Alternatively or in addition, where observable measurements have not been obtained, the expected maximum drift at a temperature and relative humidity may be interpolated or extrapolated based on the existing drift data. Every CO sensor may exhibit differing drift characteristics, and a statistically significant set of CO sensors, such as 60 or more, may be tested to better understand the range of variation. Once the expected maximum amount of drift can be determined for each temperature and relative humidity, a corresponding upper_limit value may be selected such that the processor 105 cannot compensate for more sensor drift than would be expected at the temperature and relative humidity.

Referring back to FIG. 2B, it should be appreciated that any number (N) of determinations may be made be made of the ambient environmental conditions as shown in step 260, and that any number of corrective formulas (N) may be applied based on the outcome of those determinations as shown in step 265. This may be useful, for example, to have very precisely-controlled drift adjustments, which may be linked to ambient environmental conditions to allow for a common drift adjustment scheme to be used regardless of the specific effect that different conditions may have on different sensors. For example, two sensors provided by the same manufacturer and with the same expected drift may actually exhibit different ranges or degrees of drift in some or all ambient operating conditions. Techniques as disclosed herein allow for adjustment of measurements made by such sensors.

Figure 3A:
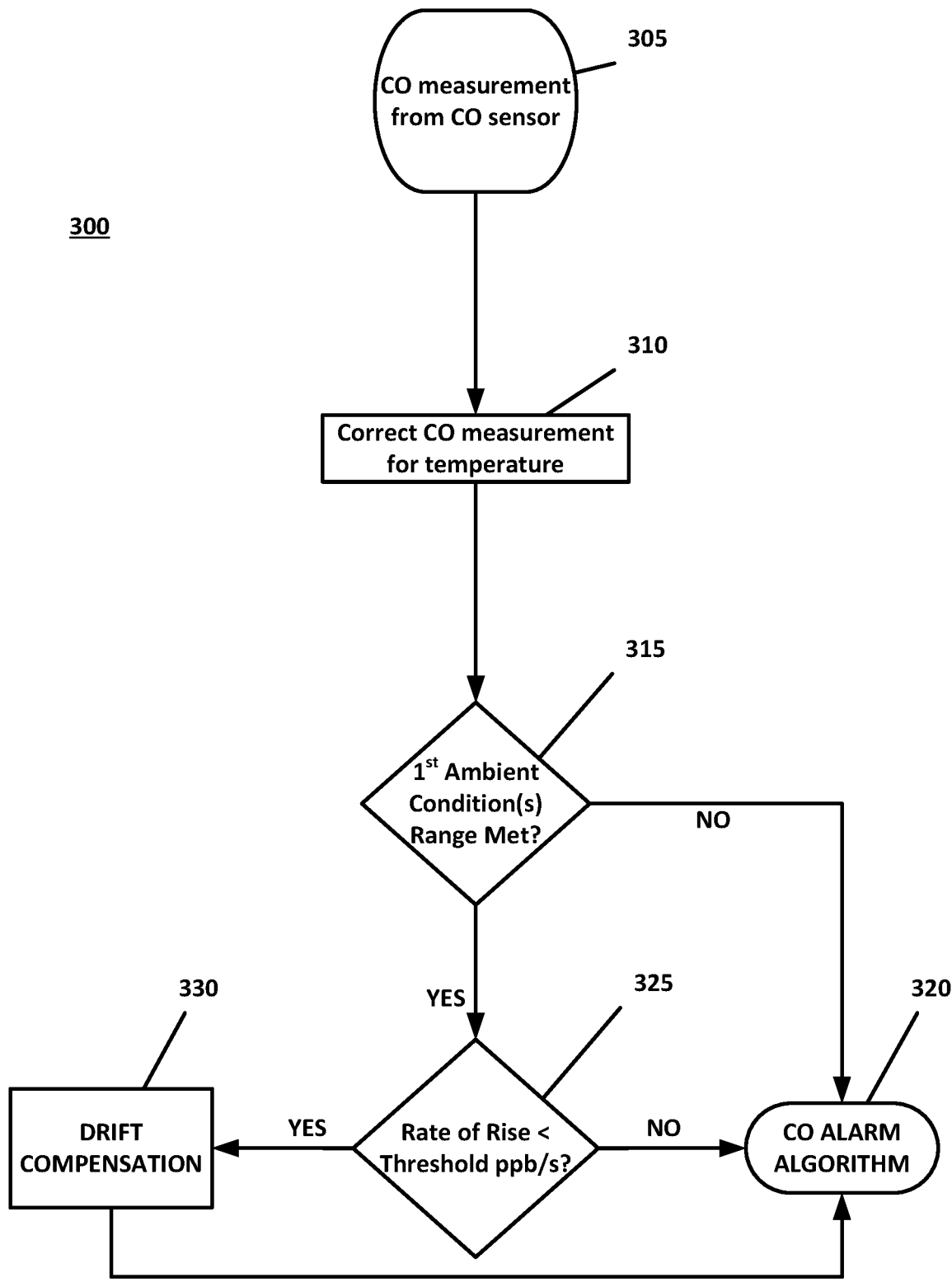
FIGS. 3A and 3B are a flow diagram illustrating an example of a method for identifying and compensating for drift of a sensor according to an embodiment of the disclosed subject matter.
Figure 3B:
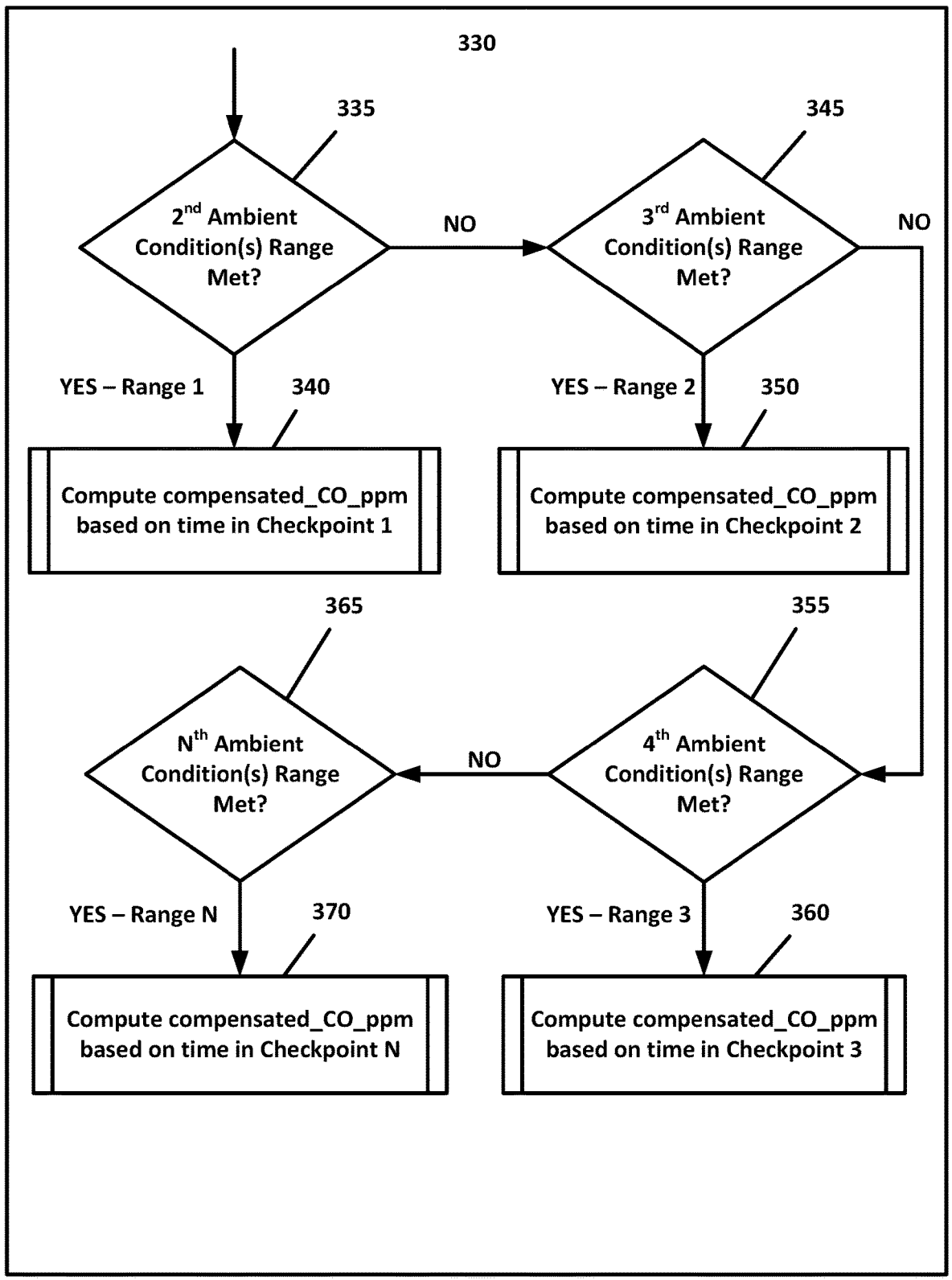

Alternatively or in addition to the baseline correction technique described with respect to FIG. 2, time-based adjustment techniques also may be used. FIGS. 3A and 3B are flow diagrams illustrating an example method 300 for compensating for drift of a CO sensor using a time-based bucketing approach. In the method 300 as shown in FIG. 3A, a CO measurement 305 is obtained from the CO sensor 120. The measurement 305 may be received by the processor 105 and may be a voltage reading, a current reading, a packetized message, or other means of signaling known in the art. The CO measurement 305 may be corrected for temperature at step 310 by applying a compensation factor to the current CO measurement 305, as previously disclosed with respect to FIG. 2A. The compensation factor used to calculate the corrected measurement may be supplied by the sensor manufacturer or determined experimentally. At step 315, the processor 105 may determine whether the current ambient conditions fall within a first range, such as a range within which it is expected that the sensor may be susceptible to drift. As a specific example, it may be expected that the sensor will not exhibit drift when either the ambient temperature is 26° C. or less or the ambient relative humidity is 75% or less. In this example, then, the processor 105 will proceed to carry out the CO alarm algorithm 320 when such conditions are present. If it is determined that ambient conditions are such that the sensor may be expected to exhibit appreciable drift, then the method may continue to determine the degree of drift present. Continuing the example above and as shown in FIG. 3A, if the ambient temperature is greater than 26° C. and the ambient relative humidity is greater than 75%, the method proceeds to step 325 where the rate at which the CO sensor 120 reading is rising is assessed to determine whether it is less than a selected threshold amount. For example, the threshold amount may be selected to fall within a range of 6-16 ppb/s. If the rate of rise is less than the selected threshold, then the processor 105 proceeds to the drift compensation block 330. Otherwise, it may be presumed that the CO sensor 120 reading is accurate, and the method proceeds to the CO alarm algorithm 320.

FIG. 3B illustrates the details of drift compensation block 330. Once the processor 105 enters drift compensation block 330, any number of determinations may be made of the ambient environmental conditions, and any number of corrective formulas may be applied based on the outcome of those determinations. For example, a first determination 335 may be made as to whether the ambient temperature is greater than 30° C. and whether the ambient relative humidity is greater than 90%. This operating region may be known as Range 1. If so, the CO sensor measurement is recalculated at step 340 according to formula (3) shown below. Step 340 may compute a new drift-compensated CO measurement by subtracting the smaller of, i.e., the minimum, of an upper limit value (upper_limit) multiplied by the number of minutes that the hazard detection device 100 has been operating in Range 1 divided by a drift interval (drift_interval) from the temperature-corrected CO measurement computed in step 310 (temperature_corrected_ppm). The drift interval may correspond to a known period after which time the sensor drift will have stabilized. The drift interval may be determined experimentally and may depend on the particular sensor used, the ambient temperature, and the relative humidity. The computation performed in step 340 to determine the new drift-compensated CO measurement (compensated_CO_ppm) may be expressed as follows:

$$\text{compensated\_CO\_ppm} = \text{temperature\_corrected\_ppm} - \text{MIN}[(5*\text{minutes since Range 1})/\text{drift\_interval}, \text{upper\_limit}] \quad (3)$$

The upper_limit value in formula (3) above for the temperature range tested in step 335 may be set to 5 ppm. The upper_limit value may establish a maximum amount of compensation for drift and thereby reduce the likelihood of overcompensation. Overcompensation for drift may result in the CO detection device failing to alert when the actual CO concentration has reached a dangerous level. The upper_limit value may be determined experimentally for each temperature and relative humidity by recording a maximum amount of observed drift and by setting the upper_limit to the same value. For example, at a temperature of 40° C., the maximum drift for a statistically significant set of sample CO sensors may be experimentally found to be 18, 10, 9, and 7.5 ppm at 93%, 84%, 81%, and 78% relative humidity, respectively. Accordingly, a lookup table may be constructed that associates the observed maximum drift amount at each temperature and relative humidity measurement. The lookup table may list each temperature and humidity in 0.1, 1, 5, 10, or any other unit increment according to the granularity desired. Alternatively or in addition, where observable measurements have not been obtained, the expected maximum drift at a temperature and relative humidity may be interpolated or extrapolated based on the existing drift data. Every CO sensor may exhibit differing drift characteristics, and a statistically significant set of CO sensors, such as 60 or more, may be tested to better understand the range of variation. Once the expected maximum amount of drift can be determined for each temperature and relative humidity, a corresponding upper_limit value may be selected such that the processor 105 cannot compensate for more sensor drift than would be expected at the temperature and relative humidity.

More generally, techniques as disclosed herein may compensate for observed or expected drift when the sensor is operating in an environment in which drift is expected to occur by adjusting the measured CO value by a fixed amount, a computed drift amount, or a combination thereof.

This basic process of determining ambient operating conditions of the sensor and making an adjustment accordingly may be repeated any number of times. For example, referring back to FIG. 3B, a second determination 345 may be made as to whether the ambient temperature is between 25° C. and 30° C., and whether the ambient relative humidity is greater than 75%. This operating region may be known as Range 2. If so, the CO measurement is recalculated at step 350 according to formula (4) shown below. Step 350 may compute a new drift-compensated CO measurement by subtracting the smaller of, i.e., the minimum, of an upper limit value (upper_limit) multiplied by the number of minutes that the hazard detection device 100 has been operating in Range 2 divided by a drift interval (drift_interval) from the temperature-corrected CO measurement computed in step 310 (temperature_corrected_ppm). The drift interval may correspond to a known period after which time the sensor drift will have stabilized. The drift interval may be determined experimentally and may depend on the particular sensor used, the ambient temperature, and the relative humidity. The computation performed in step 350 to determine the new drift-compensated CO measurement (compensated_CO_ppm) may be expressed as follows:

$$\text{compensated\_CO\_ppm} = \text{temperature\_corrected\_ppm} - \text{MIN}[(2*\text{minutes since Range 2})/\text{drift\_interval}, \text{upper\_limit}] \quad (4)$$

The upper_limit value in formula (4) above for the temperature range tested in step 345 may be set to 2 ppm. The upper_limit value may establish a maximum amount of compensation for drift and thereby reduce the likelihood of overcompensation. Overcompensation for drift may result in the CO detection device failing to alert when the actual CO concentration has reached a dangerous level. The upper_limit value may be determined experimentally for each temperature and relative humidity by recording a maximum amount of observed drift and by setting the upper_limit to the same value. For example, at a temperature of 40° C., the maximum drift for a statistically significant set of sample CO sensors may be experimentally found to be 18, 10, 9, and 7.5 ppm at 93%, 84%, 81%, and 78% relative humidity, respectively. Accordingly, a lookup table may be constructed that associates the observed maximum drift amount at each temperature and relative humidity measurement. The lookup table may list each temperature and humidity in 0.1, 1, 5, 10, or any other unit increment according to the granularity desired. Alternatively or in addition, where observable measurements have not been obtained, the expected maximum drift at a temperature and relative humidity may be interpolated or extrapolated based on the existing drift data. Every CO sensor may exhibit differing drift characteristics, and a statistically significant set of CO sensors, such as 60 or more, may be tested to better understand the range of variation. Once the expected maximum amount of drift can be determined for each temperature and relative humidity, a corresponding upper_limit value may be selected such that the processor 105 cannot compensate for more sensor drift than would be expected at the temperature and relative humidity.

Referring back to FIG. 3B, a third determination 355 may be made as to whether the ambient temperature is between 30° C. and 35° C., and whether the ambient relative humidity is greater than 75%. This operating region may be known as Range 3. If so, the CO measurement is recalculated at step 360 according to formula (5) shown below. Step 360 may compute a new drift-compensated CO measurement by subtracting the smaller of, i.e., the minimum, of an upper limit value (upper_limit) multiplied by the number of minutes that the hazard detection device 100 has been operating in Range 3 divided by a drift interval (drift_interval) from the temperature-corrected CO measurement computed in step 310 (temperature_corrected_ppm). The drift interval may correspond to a known period after which time the sensor drift will have stabilized. The drift interval may be determined experimentally and may depend on the particular sensor used, the ambient temperature, and the relative humidity. The computation performed in step 360 to determine the new drift-compensated CO measurement (compensated_CO_ppm) may be expressed as follows:

$$\text{compensated\_CO\_ppm} = \text{temperature\_corrected\_ppm} - \text{MIN}[(5 * \text{minutes since Range 3})/\text{drift\_interval}, \text{upper\_limit}] \quad (5)$$

The upper_limit value in formula (5) above for the temperature range tested in step 355 may be set to 5 ppm. The upper_limit value may establish a maximum amount of compensation for drift and thereby reduce the likelihood of overcompensation. Overcompensation for drift may result in the CO detection device failing to alert when the actual CO concentration has reached a dangerous level. The upper_limit value may be determined experimentally for each temperature and relative humidity by recording a maximum amount of observed drift and by setting the upper_limit to the same value. For example, at a temperature of 40° C., the maximum drift for a statistically significant set of sample CO sensors may be experimentally found to be 18, 10, 9, and 7.5 ppm at 93%, 84%, 81%, and 78% relative humidity, respectively. Accordingly, a lookup table may be constructed that associates the observed maximum drift amount at each temperature and relative humidity measurement. The lookup table may list each temperature and humidity in 0.1, 1, 5, 10, or any other unit increment according to the granularity desired. Alternatively or in addition, where observable measurements have not been obtained, the expected maximum drift at a temperature and relative humidity may be interpolated or extrapolated based on the existing drift data. Every CO sensor may exhibit differing drift characteristics, and a statistically significant set of CO sensors, such as 60 or more, may be tested to better understand the range of variation. Once the expected maximum amount of drift can be determined for each temperature and relative humidity, a corresponding upper_limit value may be selected such that the processor 105 cannot compensate for more sensor drift than would be expected at the temperature and relative humidity.

Referring back to FIG. 3B, it should be appreciated that any number (N) of determinations may be made be made of the ambient environmental conditions as shown in step 365, and that any number of corrective formulas (N) may be applied based on the outcome of those determinations as shown in step 370. This may be useful, for example, to have very precisely-controlled drift adjustments, which may be linked to ambient environmental conditions to allow for a common drift adjustment scheme to be used regardless of the specific effect that different conditions may have on different sensors. For example, two sensors provided by the same manufacturer and with the same expected drift may actually exhibit different ranges or degrees of drift in some or all ambient operating conditions. Techniques as disclosed herein allow for adjustment of measurements made by such sensors.

It should be appreciated that the method steps illustrated in FIGS. 2A, 2B, 3A, and 3B are not limited to their respective flow diagrams, and may be selectively added, omitted, merged, or otherwise commingled to achieve the desired drift compensation model characteristics.

Embodiments disclosed herein may use one or more sensors. In general, a "sensor" may refer to any device that can obtain information about its environment. Sensors may be described by the type of information they collect. For example, sensor types as disclosed herein may include sensors to detect motion, smoke, carbon monoxide, proximity, temperature, time, physical orientation, acceleration, location, entry, presence, pressure, light, sound, and the like. A sensor also may be described in terms of the particular physical device that obtains the environmental information. For example, an accelerometer may obtain acceleration information, and thus may be used as a general motion sensor and/or an acceleration sensor. A sensor also may be described in terms of the specific hardware components used to implement the sensor. For example, a temperature sensor may include a thermistor, thermocouple, resistance temperature detector, integrated circuit temperature detector, or combinations thereof. A sensor also may be described in terms of a function or functions the sensor performs within an integrated sensor network, such as a smart home environment as disclosed herein. For example, a sensor may operate as a security sensor when it is used to determine security events such as unauthorized entry. A sensor may operate with different functions at different times, such as where a motion sensor is used to control lighting in a smart home environment when an authorized user is present and is used to alert to unauthorized or unexpected movement when no authorized user is present, or when an alarm system is in an "armed" state, or the like. In some cases, a sensor may operate as multiple sensor types sequentially or concurrently, such as where a temperature sensor is used to detect a change in temperature, as well as the presence of a person or animal. A sensor also may operate in different modes at the same or different times. For example, a sensor may be configured to operate in one mode during the day and another mode at night. As another example, a sensor may operate in different modes based upon a state of a home security system or a smart home environment, or as otherwise directed by such a system.

In general, a "sensor" as disclosed herein may include multiple sensors or sub-sensors, such as where a position sensor includes both a global positioning sensor (GPS) as well as a wireless network sensor, which provides data that can be correlated with known wireless networks to obtain location information. Multiple sensors may be arranged in a single physical housing, such as where a single device includes movement, temperature, magnetic, and/or other sensors. Such a housing also may be referred to as a sensor or a sensor device. For clarity, sensors are described with respect to the particular functions they perform, and/or the particular physical hardware used, when such specification is necessary for understanding of the embodiments disclosed herein.

Figure 5:
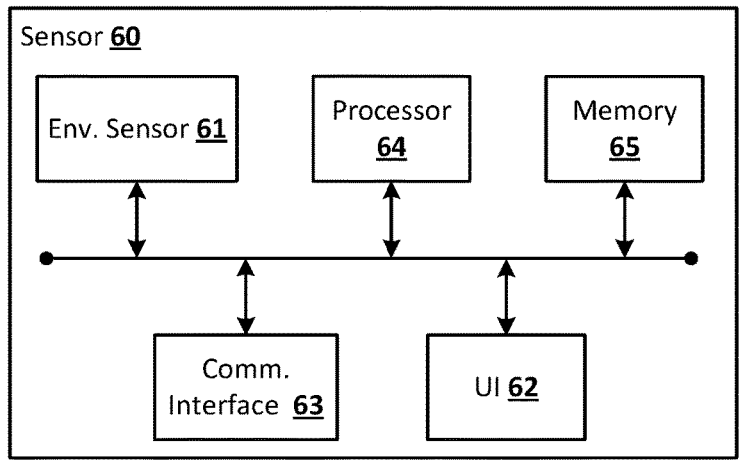
FIG. 5 shows a system according to an embodiment of the disclosed subject matter.

A sensor may include hardware in addition to the specific physical sensor that obtains information about the environment. FIG. 5 shows an example sensor as disclosed herein. The sensor 60 may include an environmental sensor 61, such as a temperature sensor, smoke sensor, carbon monoxide sensor, motion sensor, accelerometer, proximity sensor, passive infrared (PIR) sensor, magnetic field sensor, radio frequency (RF) sensor, light sensor, relative humidity sensor, pressure sensor, microphone, or any other suitable environmental sensor, that obtains a corresponding type of information about the environment in which the sensor 60 is located. The sensor shown in FIG. 5 may be a CO sensor as previously described with respect to FIG. 1, or it may incorporate some or all of the components shown in and described with respect to FIG. 1. A processor 64 may receive and analyze data obtained by the sensor 61, control operation of other components of the sensor 60, and process communication between the sensor and other devices. The processor 64 may execute instructions stored on a computer-readable memory 65. The memory 65 or another memory in the sensor 60 may also store environmental data obtained by the sensor 61. A communication interface 63, such as a wi-fi or other wireless interface, Ethernet or other local network interface, or the like may allow for communication by the sensor 60 with other devices. A user interface (UI) 62 may provide information and/or receive input from a user of the sensor. The UI 62 may include, for example, a speaker to output an audible alarm when an event is detected by the sensor 60 and/or when triggered by another sensor or event in the system, such as the alarm algorithm 220, 320 previously described. Alternatively, or in addition, the UI 62 may include a light to be activated when an event is detected by the sensor 60. The user interface may be relatively minimal, such as a limited-output display, or it may be a full-featured interface such as a touchscreen. Components within the sensor 60 may transmit and receive information to and from one another via an internal bus or other mechanism as will be readily understood by one of skill in the art. One or more components may be implemented in a single physical arrangement, such as where multiple components are implemented on a single integrated circuit. Sensors as disclosed herein may include other components, and/or may not include all of the illustrative components shown.

Data generated by one or more sensors may indicate patterns in the behavior of one or more users and/or an environment state over time, and thus may be used to "learn" such characteristics. For example, data generated by an ambient light sensor in a room of a house and the time of day may be stored in a local or remote storage medium with the permission of an end user. A processor in communication with the storage medium may compute a behavior based on the data generated by the light sensor. The light sensor data may indicate that the amount of light detected increases until an approximate time or time period, such as 3:30 PM, and then declines until another approximate time or time period, such as 5:30 PM, at which point there is an abrupt increase in the amount of light detected. In many cases, the amount of light detected after the second time period may be either below a dark level of light (e.g., under or equal to 60 lux) or bright (e.g., equal to or above 400 lux). In this example, the data may indicate that after 5:30 PM, an occupant is turning on/off a light as the occupant of the room in which the sensor is located enters/leaves the room. At other times, the light sensor data may indicate that no lights are turned on/off in the room. The system, therefore, may learn that the occupants' patterns of turning on and off lights, and may generate a response to the learned behavior. For example, at 5:30 PM, a smart home environment or other sensor network may automatically activate the lights in the room if it detects an occupant in proximity to the home. In some embodiments, such behavior patterns may be verified using other sensors. Continuing the example, user behavior regarding specific lights may be verified and/or further refined based upon states of, or data gathered by, smart switches, outlets, lamps, and the like.

Sensors as disclosed herein may operate within a communication network, such as a conventional wireless network, and/or a sensor-specific network through which sensors may communicate with one another and/or with dedicated other devices. In some configurations one or more sensors may provide information to one or more other sensors, to a central controller, or to any other device capable of communicating on a network with the one or more sensors. A central controller may be general- or special-purpose. For example, one type of central controller is a home automation network, that collects and analyzes data from one or more sensors within the home. Another example of a central controller is a special-purpose controller that is dedicated to a subset of functions, such as a security controller that collects and analyzes sensor data primarily or exclusively as it relates to various security considerations for a location. A central controller may be located locally with respect to the sensors with which it communicates and from which it obtains sensor data, such as in the case where it is positioned within a home that includes a home automation and/or sensor network. Alternatively, or in addition, a central controller as disclosed herein may be remote from the sensors, such as where the central controller is implemented as a cloud-based system that communicates with multiple sensors, which may be located at multiple locations and may be local or remote with respect to one another.

Figure 6:
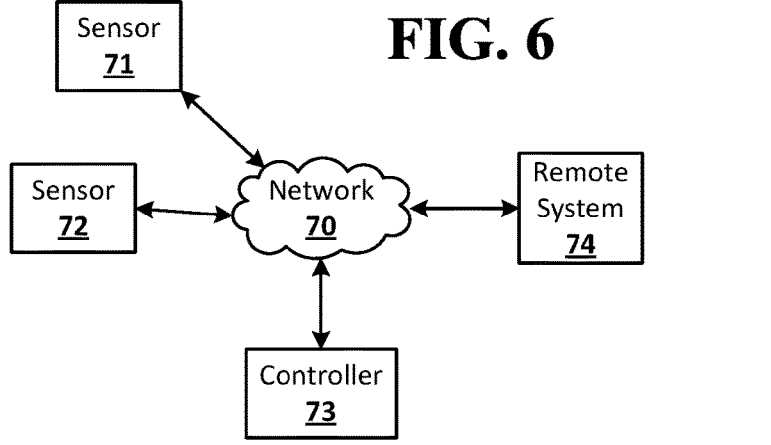
FIG. 6 shows a system according to an embodiment of the disclosed subject matter.
Figure 7:
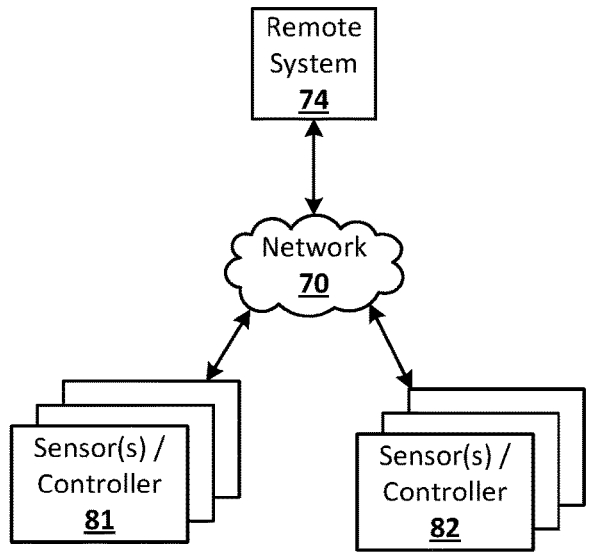
FIG. 7 shows a system according to an embodiment of the disclosed subject matter.

FIG. 6 shows an example of a sensor network as disclosed herein, which may be implemented over any suitable wired and/or wireless communication networks. One or more sensors 71, 72 may communicate via a local network 70, such as a Wi-Fi or other suitable network, with each other and/or with a controller 73. The controller may be a general- or special-purpose computer. The controller may, for example, receive, aggregate, and/or analyze environmental information received from the sensors 71, 72. The sensors 71, 72 and the controller 73 may be located locally to one another, such as within a single dwelling, office space, building, room, or the like, or they may be remote from each other, such as where the controller 73 is implemented in a remote system 74 such as a cloud-based reporting and/or analysis system. Alternatively, or in addition, sensors may communicate directly with a remote system 74. The remote system 74 may, for example, aggregate data from multiple locations, provide instruction, software updates, and/or aggregated data to a controller 73 and/or sensors 71, 72.

The sensor network shown in FIG. 6 may be an example of a smart-home environment. The depicted smart-home environment may include a structure, a house, office building, garage, mobile home, or the like. The devices of the smart home environment, such as the sensors 71, 72, the controller 73, and the network 70 may be integrated into a smart-home environment that does not include an entire structure, such as an apartment, condominium, or office space.

The smart home environment can control and/or be coupled to devices outside of the structure. For example, one or more of the sensors 71, 72 may be located outside the structure, for example, at one or more distances from the structure (e.g., sensors 71, 72 may be disposed outside the structure, at points along a land perimeter on which the structure is located, and the like. One or more of the devices in the smart home environment need not physically be within the structure. For example, the controller 73 which may receive input from the sensors 71, 72 may be located outside of the structure.

The structure of the smart-home environment may include a plurality of rooms, separated at least partly from each other via walls. The walls can include interior walls or exterior walls. Each room can further include a floor and a ceiling. Devices of the smart-home environment, such as the sensors 71, 72, may be mounted on, integrated with and/or supported by a wall, floor, or ceiling of the structure.

The smart-home environment including the sensor network shown in FIG. 6 may include a plurality of devices, including intelligent, multi-sensing, network-connected devices, that can integrate seamlessly with each other and/or with a central server or a cloud-computing system (e.g., controller 73 and/or remote system 74) to provide home-security and smart-home features. The smart-home environment may include one or more intelligent, multi-sensing, network-connected thermostats (e.g., "smart thermostats"), one or more intelligent, network-connected, multi-sensing hazard detection units (e.g., "smart hazard detectors"), and one or more intelligent, multi-sensing, network-connected entryway interface devices (e.g., "smart doorbells"). The smart hazard detectors, smart thermostats, and smart doorbells may be the sensors 71, 72 shown in FIG. 6.

For example, a smart thermostat may detect ambient climate characteristics (e.g., temperature and/or relative humidity) and may control an HVAC (heating, ventilating, and air conditioning) system accordingly of the structure. For example, the ambient client characteristics may be detected by sensors 71, 72 shown in FIG. 6, and the controller 73 may control the HVAC system (not shown) of the structure.

As another example, a smart hazard detector may detect the presence of a hazardous substance or a substance indicative of a hazardous substance (e.g., smoke, fire, or carbon monoxide). For example, smoke, fire, and/or carbon monoxide may be detected by sensors 71, 72 shown in FIG. 6, and the controller 73 may control an alarm system to provide a visual and/or audible alarm to the user of the smart-home environment.

As another example, a smart doorbell may control doorbell functionality, detect a person's approach to or departure from a location (e.g., an outer door to the structure), and announce a person's approach or departure from the structure via audible and/or visual message that is output by a speaker and/or a display coupled to, for example, the controller 73.

In some embodiments, the smart-home environment of the sensor network shown in FIG. 6 may include one or more intelligent, multi-sensing, network-connected wall switches (e.g., "smart wall switches"), one or more intelligent, multi-sensing, network-connected wall plug interfaces (e.g., "smart wall plugs"). The smart wall switches and/or smart wall plugs may be or include one or more of the sensors 71, 72 shown in FIG. 6. A smart wall switch may detect ambient lighting conditions and control a power and/or dim state of one or more lights. For example, a sensor such as sensors 71, 72, may detect ambient lighting conditions, and a device such as the controller 73 may control the power to one or more lights (not shown) in the smart-home environment. Smart wall switches may also control a power state or speed of a fan, such as a ceiling fan. For example, sensors 72, 72 may detect the power and/or speed of a fan, and the controller 73 may adjusting the power and/or speed of the fan, accordingly. Smart wall plugs may control supply of power to one or more wall plugs (e.g., such that power is not supplied to the plug if nobody is detected to be within the smart-home environment). For example, one of the smart wall plugs may controls supply of power to a lamp (not shown).

In embodiments of the disclosed subject matter, a smart-home environment may include one or more intelligent, multi-sensing, network-connected entry detectors (e.g., "smart entry detectors"). Such detectors may be or include one or more of the sensors 71, 72 shown in FIG. 6. The illustrated smart entry detectors (e.g., sensors 71, 72) may be disposed at one or more windows, doors, and other entry points of the smart-home environment for detecting when a window, door, or other entry point is opened, broken, breached, and/or compromised. The smart entry detectors may generate a corresponding signal to be provided to the controller 73 and/or the remote system 74 when a window or door is opened, closed, breached, and/or compromised. In some embodiments of the disclosed subject matter, the alarm system, which may be included with controller 73 and/or coupled to the network 70 may not arm unless all smart entry detectors (e.g., sensors 71, 72) indicate that all doors, windows, entryways, and the like are closed and/or that all smart entry detectors are armed.

The smart-home environment of the sensor network shown in FIG. 6 can include one or more intelligent, multi-sensing, network-connected doorknobs (e.g., "smart doorknob"). For example, the sensors 71, 72 may be coupled to a doorknob of a door (e.g., doorknobs 122 located on external doors of the structure of the smart-home environment). However, it should be appreciated that smart doorknobs can be provided on external and/or internal doors of the smart-home environment.

The smart thermostats, the smart hazard detectors, the smart doorbells, the smart wall switches, the smart wall plugs, the smart entry detectors, the smart doorknobs, the keypads, and other devices of a smart-home environment (e.g., as illustrated as sensors 71, 72 of FIG. 6 can be communicatively coupled to each other via the network 70, and to the controller 73 and/or remote system 74 to provide security, safety, and/or comfort for the smart home environment).

A user can interact with one or more of the network-connected smart devices (e.g., via the network 70). For example, a user can communicate with one or more of the network-connected smart devices using a computer (e.g., a desktop computer, laptop computer, tablet, or the like) or other portable electronic device (e.g., a smartphone, a tablet, a key FOB, and the like). A webpage or application can be configured to receive communications from the user and control the one or more of the network-connected smart devices based on the communications and/or to present information about the device's operation to the user. For example, the user can view can arm or disarm the security system of the home.

One or more users can control one or more of the network-connected smart devices in the smart-home environment using a network-connected computer or portable electronic device. In some examples, some or all of the users (e.g., individuals who live in the home) can register their mobile device and/or key FOBs with the smart-home environment (e.g., with the controller 73). Such registration can be made at a central server (e.g., the controller 73 and/or the remote system 74) to authenticate the user and/or the electronic device as being associated with the smart-home environment, and to provide permission to the user to use the electronic device to control the network-connected smart devices and the security system of the smart-home environment. A user can use their registered electronic device to remotely control the network-connected smart devices and security system of the smart-home environment, such as when the occupant is at work or on vacation. The user may also use their registered electronic device to control the network-connected smart devices when the user is located inside the smart-home environment.

Alternatively, or in addition to registering electronic devices, the smart-home environment may make inferences about which individuals live in the home and are therefore users and which electronic devices are associated with those individuals. As such, the smart-home environment may "learn" who is a user (e.g., an authorized user) and permit the electronic devices associated with those individuals to control the network-connected smart devices of the smart-home environment (e.g., devices communicatively coupled to the network 70), in some embodiments including sensors used by or within the smart-home environment. Various types of notices and other information may be provided to users via messages sent to one or more user electronic devices. For example, the messages can be sent via email, short message service (SMS), multimedia messaging service (MMS), unstructured supplementary service data (USSD), as well as any other type of messaging services and/or communication protocols.

A smart-home environment may include communication with devices outside of the smart-home environment but within a proximate geographical range of the home. For example, the smart-home environment may include an outdoor lighting system (not shown) that communicates information through the communication network 70 or directly to a central server or cloud-computing system (e.g., controller 73 and/or remote system 74) regarding detected movement and/or presence of people, animals, and any other objects and receives back commands for controlling the lighting accordingly.

The controller 73 and/or remote system 74 can control the outdoor lighting system based on information received from the other network-connected smart devices in the smart-home environment. For example, in the event, any of the network-connected smart devices, such as smart wall plugs located outdoors, detect movement at night time, the controller 73 and/or remote system 74 can activate the outdoor lighting system and/or other lights in the smart-home environment. As another example, a carbon monoxide sensor as described herein with respect to FIG. 1 may provide data to a controller 73, which then may provide an indication of the CO in the smart-home environment by indicating that the measured level is acceptable, or by sounding an alarm or other alert when the CO level is considered unacceptable. That is, the alarm algorithms 220, 320 previously described may be implemented by or with a smart-home system as shown in FIG. 6, such as where a central controller 73 and/or a remote system 74 execute or enable portions of the algorithm.

In some configurations, a remote system 74 may aggregate data from multiple locations, such as multiple buildings, multi-resident buildings, individual residences within a neighborhood, multiple neighborhoods, and the like. In general, multiple sensor/controller systems 81, 82 as previously described with respect to FIG. 6 may provide information to the remote system 74. The systems 81, 82 may provide data directly from one or more sensors as previously described, or the data may be aggregated and/or analyzed by local controllers such as the controller 73, which then communicates with the remote system 74. The remote system may aggregate and analyze the data from multiple locations and may provide aggregate results to each location. For example, the remote system 74 may examine larger regions for common sensor data or trends in sensor data and provide information on the identified commonality or environmental data trends to each local system 81, 82.

Figure 4:
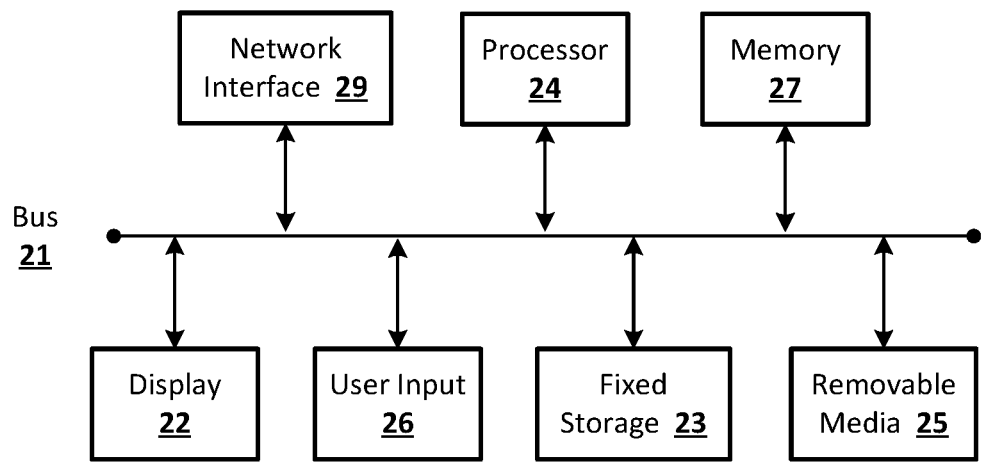
FIG. 4 shows a computing device according to an embodiment of the disclosed subject matter.

Embodiments of the presently disclosed subject matter may be implemented in and used with a variety of computing devices. FIG. 4 is an example computing device 20 suitable for implementing embodiments of the presently disclosed subject matter. For example, the device 20 may be used to implement a controller, a device including sensors as disclosed herein, or the like. Alternatively, or in addition, the device 20 may be, for example, a desktop or laptop computer, or a mobile computing device such as a smart phone, tablet, or the like. The device 20 may include a bus 21 which interconnects major components of the computer 20, such as a central processor 24, a memory 27 such as Random Access Memory (RAM), Read Only Memory (ROM), flash RAM, or the like, a user display 22 such as a display screen, a user input interface 26, which may include one or more controllers and associated user input devices such as a keyboard, mouse, touch screen, and the like, a fixed storage 23 such as a hard drive, flash storage, and the like, a removable media component 25 operative to control and receive an optical disk, flash drive, and the like, and a network interface 29 operable to communicate with one or more remote devices via a suitable network connection.

The bus 21 allows data communication between the central processor 24 and one or more memory components 25, 27, which may include RAM, ROM, and other memory, as previously noted. Applications resident with the computer 20 are generally stored on and accessed via a computer readable storage medium.

The fixed storage 23 may be integral with the computer 20 or may be separate and accessed through other interfaces. The network interface 29 may provide a direct connection to a remote server via a wired or wireless connection. The network interface 29 may provide such connection using any suitable technique and protocol as will be readily understood by one of skill in the art, including digital cellular telephone, Wi-Fi, Bluetooth®, near-field, and the like. For example, the network interface 29 may allow the device to communicate with other computers via one or more local, wide-area, or other communication networks, as described in further detail herein.

Various embodiments of the presently disclosed subject matter may include or be embodied in the form of computer-implemented processes and apparatuses for practicing those processes. Embodiments also may be embodied in the form of a computer program product having computer program code containing instructions embodied in non-transitory and/or tangible media, such as hard drives, USB (universal serial bus) drives, or any other machine readable storage medium, such that when the computer program code is loaded into and executed by a computer, the computer becomes an apparatus for practicing embodiments of the disclosed subject matter. When implemented on a general-purpose microprocessor, the computer program code may configure the microprocessor to become a special-purpose device, such as by creation of specific logic circuits as specified by the instructions.

Embodiments may be implemented using hardware that may include a processor, such as a general-purpose microprocessor and/or an Application Specific Integrated Circuit (ASIC) that embodies all or part of the techniques according to embodiments of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to embodiments of the disclosed subject matter.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

The invention claimed is:

1. A method comprising:
receiving an ambient relative humidity from a relative humidity sensor;
receiving an ambient temperature from a temperature sensor;
receiving a carbon monoxide (CO) measurement from a carbon monoxide sensor;
determining that the CO measurement indicates a drift in measurement by the CO sensor by determining
a difference between a baseline CO measurement and a temperature-corrected CO measurement being above a predetermined CO measurement threshold, and
a rate at which the CO measurement reading is rising over a unit of time being below a predetermined CO rising rate; and
responsive to the determining that the CO measurement indicates the drift, calculating a corrected CO measurement based on the CO measurement and at least one ambient condition selected from the group consisting of: the ambient relative humidity, and the ambient temperature.

2. The method of claim 1, further comprising:
generating an alarm based on the corrected CO measurement.

3. The method of claim 1, wherein the corrected CO measurement is calculated based on the ambient relative humidity.

4. The method of claim 3, wherein the corrected CO measurement is calculated based on the ambient temperature.

5. The method of claim 1, wherein determining that the CO measurement indicates the drift further comprises:
determining that the ambient temperature falls within a first temperature range;
wherein the corrected CO measurement is further based on a first compensation factor.

6. The method of claim 5, wherein determining that the CO measurement indicates the drift further comprises:
determining that the ambient temperature falls within a second temperature range,
the second temperature range different from the first temperature range; and
determining whether the drift in measurement meets a threshold, and if so, calculating the corrected CO measurement based on a compensation factor.

7. The method of claim 6, wherein the drift in measurement is based on the rate of rise of the CO measurement or a difference between the CO measurement and a predetermined
baseline measurement.

8. The method of claim 6, wherein if the threshold has not been met:
calculating the corrected CO measurement based on a first correction value when the ambient temperature falls within a third temperature range, the third temperature range different from the first and second temperature ranges.

9. The method of claim 8, wherein the first correction value is based on an amount of time the CO sensor has been operating in the third temperature range.

10. The method of claim 8, wherein if the threshold has not been met:
calculating the corrected CO measurement based on a second correction value when the ambient temperature falls within a fourth temperature range, the fourth temperature range different from the first, second, and third temperature ranges.

11. The method of claim 10, wherein the second correction value is based on an amount of time the CO sensor has been operating in the fourth temperature range.

12. The method of claim 10, wherein if the threshold has not been met:
calculating the corrected CO measurement based on a third correction value when the ambient temperature falls within a fifth temperature range, the fifth temperature range different from the first, second, third, and fourth temperature ranges.

13. The method of claim 12, wherein the third correction value is based on an amount of time the CO sensor has been operating in the fifth temperature range.

14. The method of claim 6, wherein determining that the CO measurement indicates the drift further comprises:
determining that the ambient relative humidity falls within a first humidity range.

15. The method of claim 14, wherein determining that the CO measurement indicates the drift further comprises:
determining that the ambient relative humidity falls within a second humidity range, second humidity range different from the first humidity range.

16. A hazard detection device comprising:
a relative humidity sensor;
a temperature sensor;
a carbon monoxide (CO) sensor; and
a processor configured to:
determine that a CO measurement indicates a drift in measurement by the CO sensor, by determining
a difference between a baseline CO measurement and a temperature-corrected CO measurement being above a predetermined CO measurement threshold, and
a rate at which the CO measurement reading is rising over a unit of time being below a predetermined CO rising rate; and responsive to the determining that the CO measurement indicates the drift, calculate a corrected CO measurement based on the CO measurement and at least one ambient condition selected from the group consisting of: an ambient relative humidity, and an ambient temperature.

17. The hazard detection device of claim 16, further comprising:
generating an alarm based on the corrected CO measurement.

18. The hazard detection device of claim 16, wherein the corrected CO measurement is calculated based on the ambient relative humidity.

19. The hazard detection device of claim 18, wherein the corrected CO measurement is calculated based on the ambient temperature.

20. The hazard detection device of claim 16, wherein the processor is further configured to determine that the CO measurement indicates the drift in measurement by the CO sensor by:
determining that the ambient temperature falls within a first temperature range;
wherein the corrected CO measurement is further based on a first compensation factor.

21. The hazard detection device of claim 20, wherein the processor is further configured to determine that the CO measurement indicates the drift in measurement by the CO sensor by:
determining that the ambient temperature falls within a second temperature range, the second temperature range different from the first temperature range; and
determining whether the drift in measurement meets a threshold, and if so, calculating the corrected CO measurement based on a compensation factor.

22. The hazard detection device of claim 21, wherein the drift in measurement is based on the rate of rise of the CO measurement or a difference between the CO measurement and a predetermined
baseline measurement.

23. The hazard detection device of claim 21, wherein if the threshold has not been met, the processor is further configured to:
calculate the corrected CO measurement based on a first correction value when the ambient temperature falls within a third temperature range, the third temperature range different from the first and second temperature ranges.

24. The hazard detection device of claim 23, wherein the first correction value is based on the amount of time the CO sensor has been operating in the third ambient temperature range.

25. The hazard detection device of claim 23, wherein if the threshold has not been met, the processor is further configured to:
calculate the corrected CO measurement based on a second correction value when the ambient temperature falls within a fourth temperature range, the fourth temperature range different from the first, second, and third temperature ranges.

26. The hazard detection device of claim 25, wherein the second correction value is based on an amount of time the CO sensor has been operating in the fourth temperature range.

27. The hazard detection device of claim 25, wherein if the threshold has not been met, the processor is further configured to:
calculate the corrected CO measurement based on a third correction value when the ambient temperature falls within a fifth temperature range, the fifth temperature range different from the first, second, third, and fourth temperature ranges.

28. The hazard detection device of claim 27, wherein the third correction value is based on an amount of time the CO sensor has been operating in the fifth temperature range.

29. The hazard detection device of claim 21, wherein the processor is further configured to determine that the CO measurement indicates the drift in measurement by the CO sensor by:
determining that the ambient relative humidity falls within a first humidity range.

30. The hazard detection device of claim 29, wherein the processor is further configured to determine that the CO measurement indicates the drift in measurement by the CO sensor by:
determining that the ambient relative humidity falls within a second humidity range, second humidity range different from the first humidity range.

* * * * *